US008548123B2

(12) United States Patent
He (10) Patent No.: US 8,548,123 B2
(45) Date of Patent: Oct. 1, 2013

(54) METHOD AND APPARATUS FOR USING AN AREA X-RAY DETECTOR AS A POINT DETECTOR IN AN X-RAY DIFFRACTOMETER

(75) Inventor: Bob Baoping He, Madison, WI (US)

(73) Assignee: Bruker AXS, Inc., Madison, WI (US)

( * ) Notice: Subject to any disclaimer, the term of this patent is extended or adjusted under 35 U.S.C. 154(b) by 427 days.

(21) Appl. No.: 12/769,837

(22) Filed: Apr. 29, 2010

(65) Prior Publication Data

US 2011/0268251 A1    Nov. 3, 2011

(51) Int. Cl.
*G01N 23/20*    (2006.01)
(52) U.S. Cl.
USPC .............................................. 378/73; 378/71
(58) Field of Classification Search
USPC ...................................................... 378/70–85
See application file for complete search history.

(56) References Cited

U.S. PATENT DOCUMENTS

| 7,123,686 B2 * | 10/2006 | Sakata .............................. 378/71 |
| 2007/0003012 A1 * | 1/2007 | Taguchi et al. .................. 378/71 |
| 2008/0084964 A1 * | 4/2008 | Dosho et al. ..................... 378/71 |

* cited by examiner

*Primary Examiner* — Hoon Song
(74) *Attorney, Agent, or Firm* — Robic, LLP (57) ABSTRACT

An area detector used in a two-dimensional system is used as a point detector in Bragg-Brentano and other geometries by providing the area detector with a mask the limits the area through which X-rays can enter the detector. Secondary X-ray optics and a monochromator that are part of the diffractometer geometry are attached to the area detector mask to allow a fast and easy switch between the two-dimensional detector mode and the point detector mode. A concave detector mask is used with a spherical detector in order to reduce the secondary beam path and increase detector efficiency and the opening in the detector mask can be offset from the mask center to achieve high 2θ angle measurements. Single channel bypath electronics are used to disregard the dimensional position of each X-ray count to increase the efficiency and speed of the system.

18 Claims, 6 Drawing Sheets

METHOD AND APPARATUS FOR USING AN AREA X-RAY DETECTOR AS A POINT DETECTOR IN AN X-RAY DIFFRACTOMETER

BACKGROUND

X-ray diffraction is a non-destructive technique for the qualitative and quantitative analysis of crystalline material samples, which are generally provided in the form of single crystals or powders. In accordance with this technique, an X-ray beam is generated by an X-ray tube with a stationary anode, by a conventional rotating anode X-ray source or by a synchrotron source and directed toward the material sample under investigation.

When the X-ray beam strikes the sample, the X-rays produce Bragg angle reflections from the parallel and equally spaced atomic planes in the crystalline substance. Diffraction occurs if the path of the X-rays reflected by successive planes is a multiple of the X-ray wavelength. Therefore, the spacing between the atomic planes of a crystal can be determined by detecting the diffracted X-rays and measuring the first-order angles of diffraction. These measurements are usually performed by rotating the crystalline sample while taking diffraction measurements with a point X-ray detector.

Figure 1:
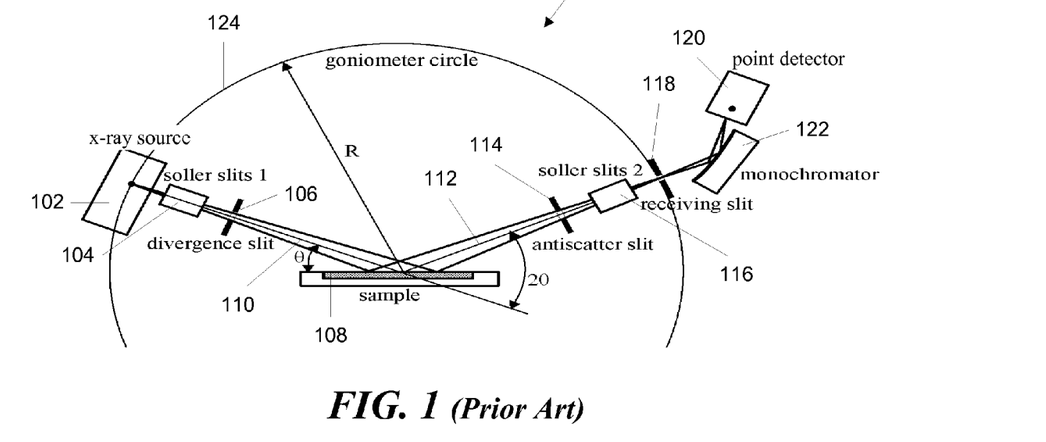
FIG. 1 is a schematic diagram of an X-ray diffractometer that uses a conventional Bragg-Brentano parafocusing geometry.

Most conventional X-ray diffractometers use a Bragg-Brentano parafocusing geometry 100 such as that shown in FIG. 1. A divergent line-focus beam from the X-ray source 102 passes first through soller slits 1 (104) and the divergence slit 106, and then hits the sample surface 108 with an incident angle θ. The incident X-rays 110 spread over the sample surface 108 with various incident angles in the vicinity of θ. The area of the irradiated region depends on the incident angle θ and beam divergence. The diffracted X-rays 112 from the irradiated area leave the sample 108 at an angle 2θ from the corresponding incident rays, pass through an anti-scatter slit 114 and soller slits 2 (116) and focus at the receiving slit 118. A point X-ray detector 120 can be mounted at a position immediately after the receiving slit 118 or after a crystal monochromator 122 as shown in FIG. 1. The X-ray source 102, soller slits 104 and divergence slit 106 are all mounted on one arm of an instrument called a goniometer (not shown in FIG. 1). Similarly, the anti-scatter slit 114, the soller slits 116, the receiving slit 118, the monochromator 122 and the point detector 120 are all mounted on a second arm of the goniometer. The arms can be rotated or scanned around an instrument center point at which the sample 108 is located.

In this geometry, the beam-spread over the sample 108 varies with the incident angle θ, but the diffracted beam 112 is focused back to the receiving slit 118 as long as the axis of the X-ray source line focus and the receiving slit 118 are at the same distance from the instrument center (the goniometer main axis). This distance, R (124), is referred to as the "goniometer circle radius".

A smaller aperture of the divergence slit 106 is used for higher 2θ resolution and a larger aperture for fast data collection. The Bragg-Brentano geometry requires that a normal to the sample surface 102 always bisect the angle between the incident beam 110 and the diffracted beam 112, that is the incident beam 110 and diffracted beam 112 are symmetric to the sample surface normal. This angular relationship can be achieved by scanning the goniometer arms at the same speed such that the angle between the X-ray source and the sample surface ($\theta_1$) always equals the angle between the X-ray detector and the sample surface ($\theta_2$) in a configuration called the "θ-θ configuration" or by holding the X-ray source stationary, rotating the sample at an angle ω and scanning the goniometer arm that holds the detector so that the angle 2θ increases at twice the speed of the angle ω in a configuration called the θ-2θ configuration.

Figure 2:
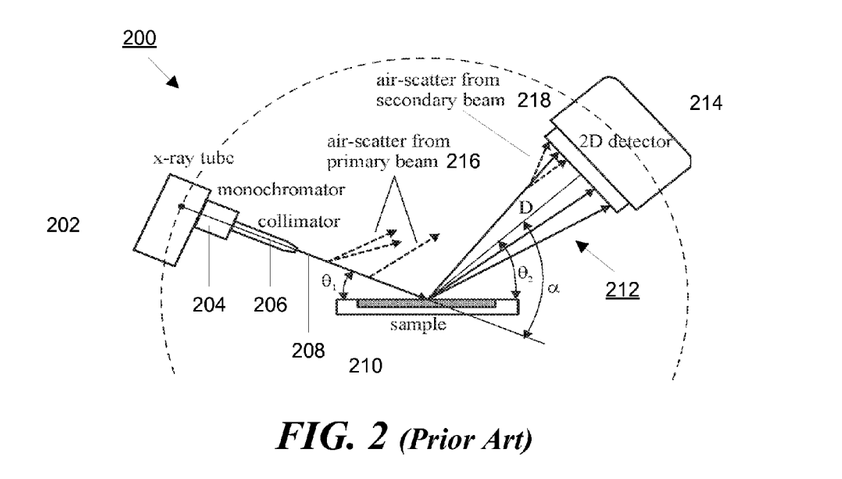
FIG. 2 is a schematic diagram of a conventional two-dimensional X-ray diffraction system that uses an area X-ray detector and corresponding data reduction and analysis to produce a two-dimensional diffraction pattern.

Two-dimensional X-ray diffraction refers to X-ray diffraction applications that use an area X-ray detector and corresponding data reduction and analysis to produce a two-dimensional diffraction pattern and is described in detail in "Two-dimensional X-ray diffraction", Bob B. He, John-Wiley and Sons, 2009. FIG. 2 shows the X-ray optics in a two-dimensional system 200 with a conventional θ-θ configuration. The X-ray tube 202, monochromator 204 and collimator assembly 206 are mounted on one of the two main axes of the system. In a conventional Bragg-Brentano diffraction system, a monochromator, such as monochromator 204, can be positioned either on the source side or the detector side, or both sides; however in a two-dimensional system, it is only possible to position the monochromator 204 on the source side. The incident beam 208 from the assembly 206 rotates about the instrument center and makes an incident angle $\theta_1$ from the sample surface 210. The first main axis of the system is also called the $\theta_1$ axis. The diffracted beams 212 travel in all directions and some are intercepted by a two dimensional detector 214 which is mounted on the other main axis of the system, $\theta_2$. The detector position is determined by the sample-to-detector distance D and the detector swing angle $\alpha(=\theta_1+\theta_2)$. In most two-dimensional diffractometers, the sample-to-detector distance can be changed manually or automatically.

In a two-dimensional X-ray diffraction system, since all, or a large portion, of the diffracted X-rays are measured simultaneously, the requirements for the X-ray optics are different from the conventional Bragg-Brentano diffractometer in many respects. In a two-dimensional system, the diffracted X-rays are measured simultaneously in a two-dimensional area so that neither the Bragg-Brentano geometry nor a conventional parallel geometry with detector soller slits can be used. The beam-spread over the sample surface cannot be focused back to the detector, so most of the time a collimated point beam is used. Therefore, X-ray optics for two-dimensional systems have different requirements in terms of the beam spectrum purity, divergence and beam cross-section profile.

In addition, a phenomenon called "air scatter" is also of more serious concern in a two-dimensional system than in a conventional diffractometer. Specifically, in diffractometers, all of the components and the space between the focal spot of the X-ray tube 202 and sample surface 210 are collectively referred to as the "primary beam path". The space between the sample surface 210 and the two-dimensional detector 214 is referred to as the "secondary beam path". The primary beam path in both conventional diffractometers and two-dimensional systems is typically sheltered by optical components except between the exit of the collimator 206 and the sample surface 210. The primary X-ray beam traveling through this open incident beam path is scattered by air in the path with two adverse effects. One is attenuation of the primary beam intensity. The more harmful effect is that the scattered X-rays travel in all directions and some reach the detector 214, as illustrated by the dotted lines 216 in FIG. 2. These scattered X-rays produce a background pattern which overlays the diffraction pattern produced by the sample. Weak diffraction patterns may be buried under the background pattern.

The diffracted X-rays are also scattered by air in the secondary beam path as indicated by the dotted lines 218 and the diffraction pattern is also both attenuated and blurred by this air scattering. However, air scatter effects from the primary beam are significantly stronger than that from secondary X-rays.

In a conventional diffractometer such as that shown in FIG. 1, an anti-scatter slit 114, diffracted beam monochromator 122 or detector soller slits 116 can be used to remove most of the air scatter not traveling in the diffracted beam direction. These measures cannot be used for a two-dimensional system, which requires an open space between the sample 210 and the two-dimensional detector 214. Radiation fluorescence is another source of intensity background in two-dimensional systems, especially when the X-ray energy of the incident beam is slightly higher than the absorption edge of the sample elements, for example, when Cu-K$_\alpha$ radiation is used for iron or ferrous alloys. In a conventional diffractometer with point detector, fluorescence can be removed by a diffracted beam monochromator 122, or an energy discrimination device, but this is not possible in two-dimensional systems.

Figure 3:
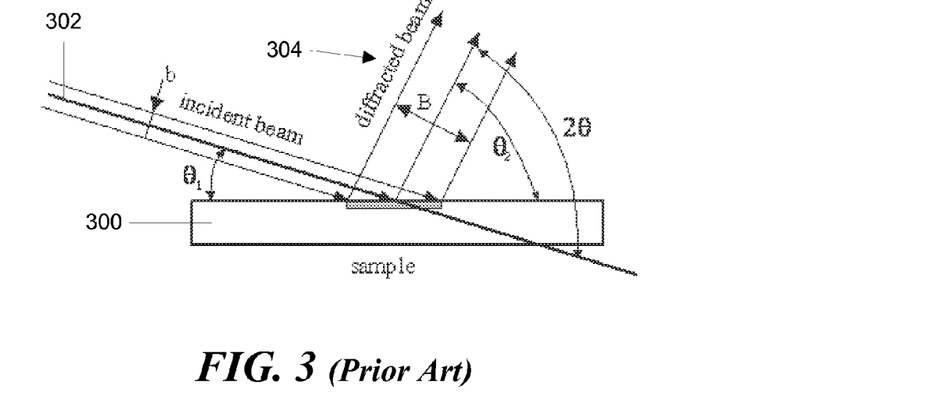
FIG. 3 is a schematic diagram of the geometry of a conventional two-dimensional diffraction system operating in reflection mode with a flat sample illustrating the defocusing effect.

Further, since the angle of the reflected X-rays cannot always be the same as the incident angle in a two-dimensional X-ray diffraction system, geometric aberrations are observed causing a defocusing effect. The defocusing effect occurs when the incident angle is lower than the reflection angle. FIG. 3 shows the geometry of two-dimensional diffraction in reflection mode with a flat sample 300. A parallel beam incident to the sample 302 is reflected and the resulting diffracted beam 304 is measured by a two-dimensional detector (not shown in FIG. 3). At low incident angles, the incident beam 302 spreads over the sample surface into an area much larger than the size of the incident X-ray beam 302. The observed diffracted beam size is magnified by the defocusing effect if the diffracted beam 304 occurs at an angle larger than the incident angle. Looking at the cross section on the diffractometer plane, the defocusing effect with reflection mode diffraction can be expressed as:

$$\frac{B}{b} = \frac{\sin\theta_2}{\sin\theta_1} = \frac{\sin(2\theta - \omega)}{\sin\omega}$$

where $\theta_1$ is the incident angle, b is the incident beam size and B is diffracted beam size. The ratio of B to b is a measurement of the geometric aberration and will be referred to as the defocusing factor. For the Bragg-Brentano parafocusing geometry discussed above, with a divergence slit 106 and a receiving slit 118 of the same size, the defocusing factor is always 1 which implies no defocusing effect.

A two-dimensional diffraction pattern contains abundant information about the atomic arrangement, microstructure and defects of a solid or liquid material. Therefore, two-dimensional X-ray diffraction is an ideal, non-destructive, analytical method for examining samples of all kinds, such as metals, polymers, ceramics, semiconductors, thin films, coatings, paints, biomaterials, composite samples for material science research, molecular structure determination and polymorphism study for drug discovery and processing, and samples with micro-volume or micro-area for forensic analysis, archaeology analysis, and homeland defense as well as many emerging applications. Accordingly, in recent years, usage of two-dimensional diffractometer has dramatically increased in academic researches and various industries and it is desirable to have a two-dimensional system available.

On the other hand, although the Bragg-Brentano geometry has a slower data acquisition rate and has less information in the resulting diffraction pattern, the higher and controllable 2θ resolution, lack of a defocusing effect, and the possibility of effective shielding from air-scatter and fluorescence discrimination by a secondary monochromator makes it desirable sometimes to use the Bragg-Brentano geometry.

Due to the various differences between the Bragg-Brentano geometry and two dimensional systems, conventionally two separate systems are required in order to acquire data under optimal conditions. However, two separate systems double the expense; require a large operating area and personnel trained in the use of both systems.

SUMMARY

In accordance with the principles of the invention, an area detector that is normally used in a two-dimensional system is used as a point detector in Bragg-Brentano and other geometries by providing the area detector with a mask the limits the area through which X-rays can enter the detector.

In one embodiment, the X-ray diffractometer is arranged in a Bragg-Brentano geometry.

In another embodiment, the X-ray diffractometer is arranged in a parallel geometry.

In yet another embodiment, the X-ray diffractometer is arranged in a grazing incident geometry.

In still another embodiment, the X-ray diffractometer is arranged in a Bragg-Brentano geometry and secondary X-ray optics that are part of the geometry are attached to the area detector mask to allow a fast and easy switch between the two-dimensional detector mode and the point detector mode.

In still another embodiment, a concave detector mask is used with a spherical detector in order to reduce the secondary beam path and increase detector efficiency.

In yet another embodiment, the opening in the detector mask is offset from the mask center to achieve high 2θ angle measurements.

In still another embodiment, a secondary monochromator is attached to the mask of an area detector with an offset opening in order to allow only desired X-ray wavelengths to reach the detector and to eliminate fluorescence.

In another embodiment, single channel bypath electronics are used with the area detector in order to disregard the dimensional position of each X-ray count to increase the efficiency and speed of the system.

DETAILED DESCRIPTION

Figure 4:
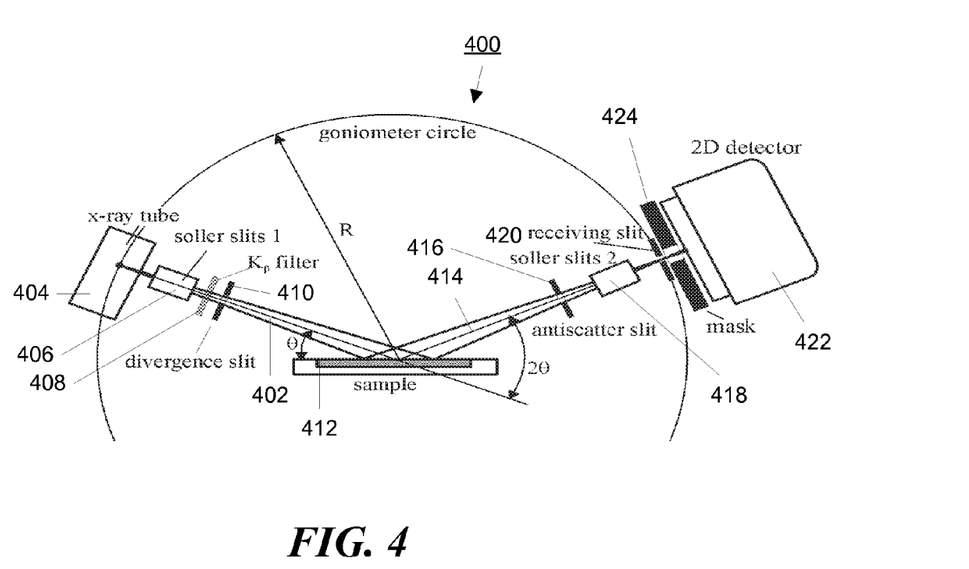
FIG. 4 is a schematic diagram of an X-ray diffractometer arranged in a Bragg-Brentano Geometry and using a two-dimensional area detector.

FIG. 4 shows an area detector used in a Bragg-Brentano Geometry 400. A divergent X-ray beam 402 from the X-ray source 404 passes first through the soller slits 1 (406), the $K_\beta$ filter 408 and the divergence slit 410 and then impinges on the sample surface 412 with an incident angle θ. The incident x-rays spread over the sample surface with various incident angles in the vicinity of θ and the area of the irradiated region depends on the incident angle θ and beam divergence.

The diffracted rays 414 from the irradiated area leave the sample surface 412 at an angle 2θ from the corresponding incident rays, pass through the anti-scatter slit 416 and soller slits 2 (418) and focus at the receiving slit 420. An area detector 422 is mounted at the position right after the receiving slit 420. A shielding mask plate 424 made from a material that is opaque to X-rays is mounted in front of the area detector 422. The mask 424 has an opening matching the size and shape of the receiving slit 420 that admits X-rays, but blocks all other X-rays from reaching the area detector 422. The blocked X-rays includes air scatter from the primary 402 or secondary 414 X-ray beams and diffracted X-ray beams that are not in the desired direction as defined by the anti-scatter slit 416 and the receiving slit 420. The function of the mask 424 is to allow only X-rays that would be measureable by a point detector to reach the area detector 422 so that the area detector 422 behaves like a point detector.

The system shown in FIG. 4 will have the function of the Bragg-Brentano diffractometer which is conventionally built with a point detector. With appropriate primary X-ray optics, the system shown in FIG. 4 can be used as a two-dimensional X-ray diffraction system by removing the secondary optics 416-420 and detector mask 424.

Figure 5:
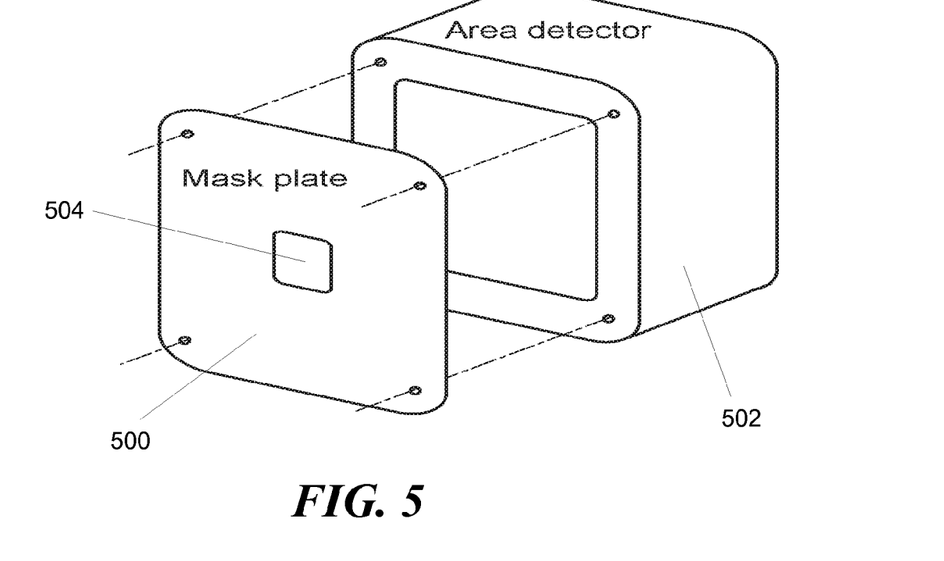
FIG. 5 is a perspective diagram of a two-dimensional detector with a detector mask.

FIG. 5 illustrates an embodiment of a two-dimensional detector mask 500 in more detail. When mounted, the mask 500, which is fabricated from radiopaque material, covers most of the active area of the detector 502 with an opening 504 to receive X-ray counts from the secondary optics of the Bragg-Brentano geometry or other diffractometer geometry typically used with a point detector. It is possible to replace the mask plate 500 with a computer program that selects only the X-ray counts from a predefined region of the two-dimensional detector 502. However, such a computer program would require that the detector to collect a two-dimensional image with specified counts for each pixel. The acquisition of an image requires each X-ray photon not only to be counted, but also to be registered for its specific position on the detector 502. This 2D image acquisition process would slow down the data acquisition as a point detector and data acquisition speed is an important specification for a point detector. Consequently, the mask 500 has distinct speed advantages.

Another important reason to use a mask, such as mask 500, is that the total detected X-ray count is limited to counts of X-rays reaching the detector through the opening. Many detectors, particularly, gaseous detectors, have limited global count rate, which is the maximum counts per unit time that can be recorded properly by a particular detector within the whole detection area. Since the mask allows X-rays to reach the detector only through the opening, the maximum count rate in the point detector mode can be as high as the maximum global count rate of the area detector.

Figure 6:
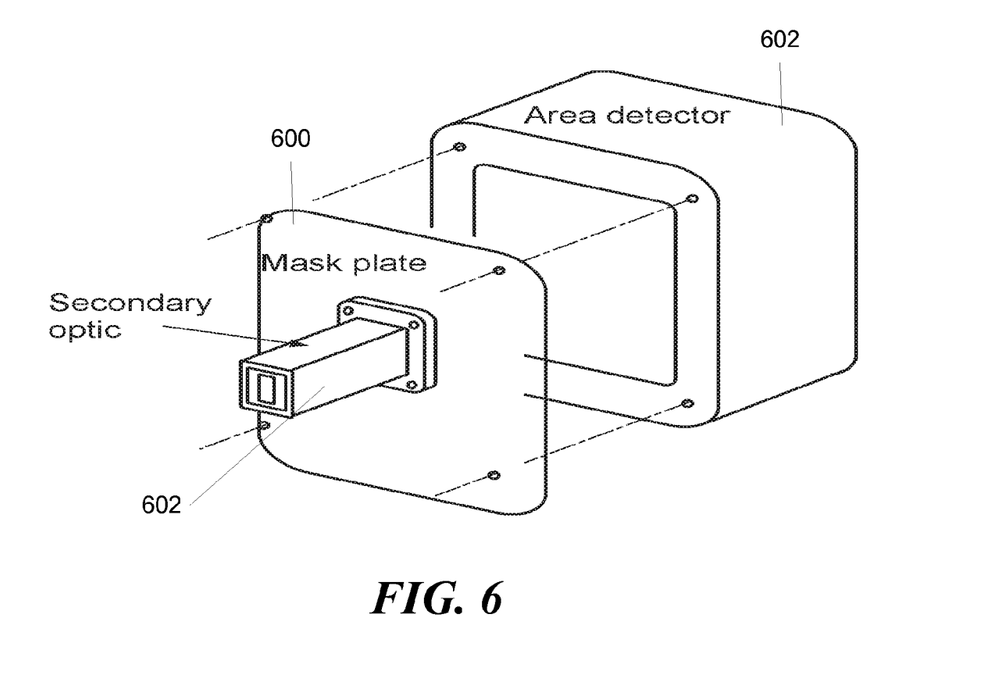
FIG. 6 is a perspective diagram of a two-dimensional detector and a detector mask having secondary X-ray optics mounted thereon.

In another embodiment shown in FIG. 6, the mask plate 600 supports the secondary optics (such as the anti-scatter slit 416, the soller slits 418 and the receiving slit 420 as shown in FIG. 4). As is shown in FIG. 6, the pre-aligned secondary optics 602 are mounted in an alignment housing that is mechanically mounted on the detector mask plate 600. This arrangement permits a fast and easy switch between the two-dimensional detector mode and the point detector mode.

Figure 7:
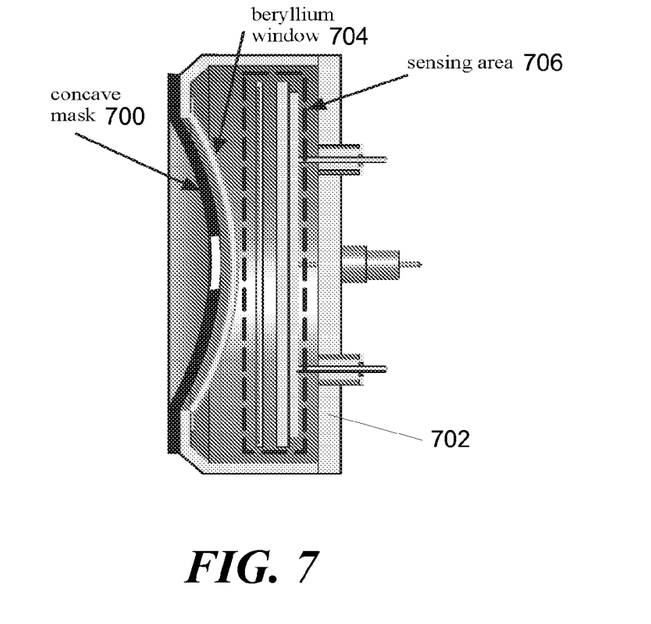
FIG. 7 is a cross-sectional diagram of showing a concave mask mounted on a gaseous area detector.

In still another embodiment, the detector mask plate can have a shape other than planar in order to fit in the secondary beam path. FIG. 7 illustrates a concave mask 700 mounted on a gaseous area detector 702. The detector 702 has a concave (spherical shaped) Beryllium window 704. The concave mask 700 allows the detector 702 to be mounted closer to the receiving slit 420 shown in FIG. 4. This feature reduces the distance between the receiving slit 420 and the sensing area 706 of the detector 702. Since, as discussed above, X-rays are attenuated by air scatter, the reduced beam path can improve the detection efficiency of the system.

Figure 8:
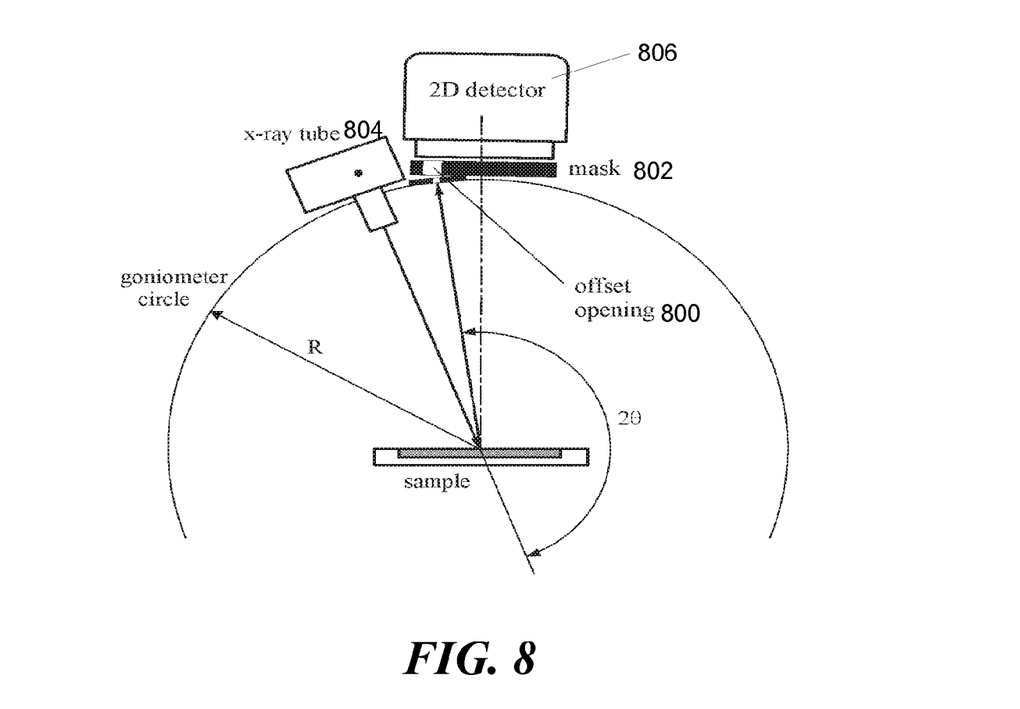
FIG. 8 is a schematic diagram of an X-ray diffractometer using an area detector as a point detector, which diagram illustrates an offset opening on the detector mask for high 2θ angle measurements.

In still another embodiment, the opening in the detector mask does not have to be in the center of the mask, for example as shown in FIGS. 5 and 6. In a diffractometer, the highest measurable 2θ angle may be limited by the size of the detector envelope and the size of the X-ray source and optics. The opening of the detector mask can be offset to one side of the detection area, so a higher 2θ angle can be measured. FIG. 8 illustrates an offset opening 800 on a detector mask 802 for high 2θ angle measurements. The X-ray tube 804 and the detector 806 are nearly in contact at the high 2θ angle measurement position and an extra 2θ angular range can be measured through the offset opening 800 on the detector mask 802. Other components, such as soller slits 406, $K_\beta$ filter 408, divergence slit 410, anti-scatter slit 416, and soller slits 418, that are shown in FIG. 4 have been omitted in this illustration in order to illustrate only a high 2θ angle capability with an offset detector mask opening. The offset opening can also be applied to the concave mask shown in FIG. 7.

Figure 9:
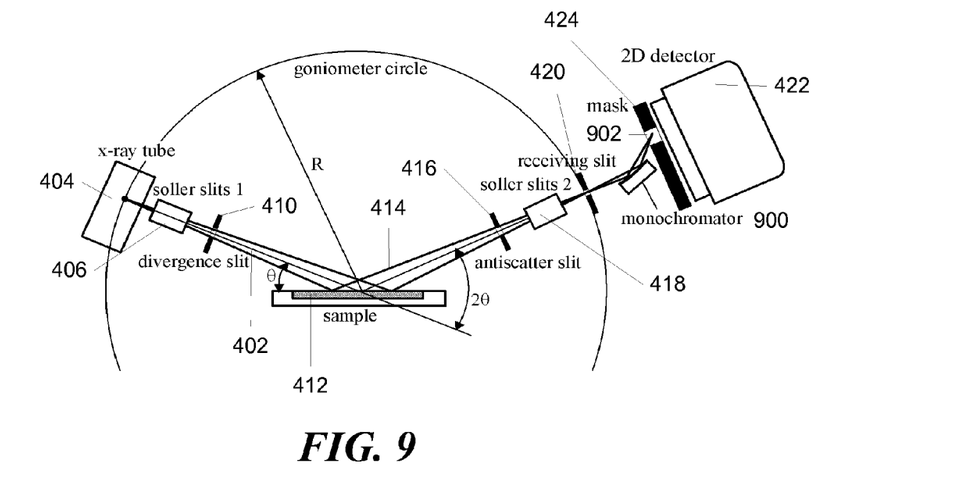
FIG. 9 is a schematic diagram of an X-ray diffractometer arranged in a Bragg-Brentano Geometry and using a two-dimensional area detector in which a crystal monochromator has been added between the receiving slit and the area detector.

In the conventional Bragg-Brentano diffractometer as illustrated in FIG. 1, a secondary monochromator 122 is used to allow only a desired X-ray wavelength, typically Kα radiation, to reach the detector 210. The fluorescence from the sample can also be removed by the secondary beam monochromator 122. A secondary monochromator can also be mounted to the area detector in a way as illustrated in FIG. 9 in order to achieve the same benefits. In FIG. 9, components that correspond to those in FIG. 4 have been given the same numerical designations. A crystal monochromator 900 has been added between the receiving slit 424 and the area detector 422. The Bragg condition requires that X-rays diffracted from the monochromator crystal 900 assume the same angle as X-rays diffracted from the sample. In this arrangement, the opening on the detector mask 902 is offset from the center of the mask to receive the X-rays diffracted from the monochromator crystal 900 and the area detector 422 should have sufficient area and be mounted close enough to the crystal 900 that the diffracted X-rays can be captured by the area detector 422 through the offset window 902.

Figure 10:
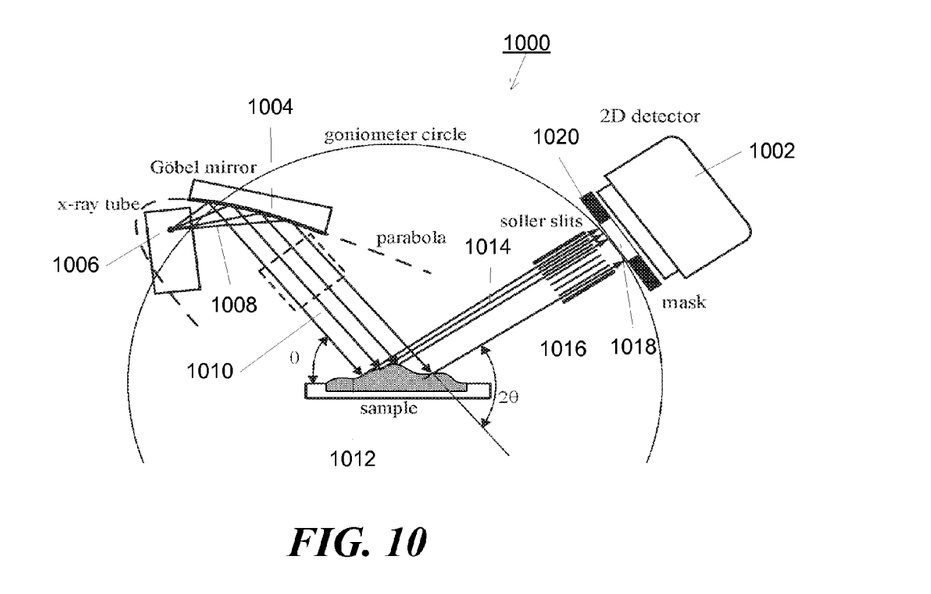
FIG. 10 illustrates a diffractometer arranged in parallel geometry with a two-dimensional detector.

The conventional Bragg-Brentano geometry is only one of the diffractometer geometry which can use an area detector configured as a point detector. In principle, all X-ray diffractometer geometries, such as parallel geometry and grazing incident geometries for reflectivity and thin film, which typically use a point X-ray detector, can use the method and apparatus in this disclosure. FIG. 10 illustrates a diffractometer in parallel geometry with a two-dimensional detector 1002. A single parabolic bent Göbel mirror 1004 transforms the divergent primary beam 1008 from the X-ray source 1006 into a parallel beam 1010. The Göbel mirror 1004 is a multilayer mirror which serves also as a monochromator, so that the incident parallel beam 1010 is a single wavelength X-ray beam. The incident x-rays spread over the sample surface 1012 with the same incident angle θ. The surface of the irradiated region can either be flat or uneven, but only the diffracted x-rays 1014 in the direction of 2θ defined by the soller slits 1016 can reach the detector 1002. In this geometry, the soller slits 1016 have an orientation different from the soller slits 418 in the Bragg-Brentano geometry. In the Bragg-Brentano geometry 400, the foils in the soller slits 418 are parallel to the diffractometer plane, while in the parallel beam geometry 1000, the foils are perpendicular to the diffractometer plane and aligned in the direction between the instrument center and detector 1002. The soller slits 1016 cover the entire opening 1018 of the detector mask 1020 so that only X-rays travelling in the same direction can reach the area detector 1002. Therefore, a diffractometer with parallel beam geometry is not sensitive to the surface roughness of the sample 1012. This is especially beneficial when collecting diffraction data from samples with a rough, uncertain or variable sample surface enclosed in an environment chamber. The same principle applies to a diffractometer with grazing incident attachment and followed by an area detector (not shown in FIG. 10).

A point detector is typically referred to as an X-ray counter with a single channel whereas an area detector can measure X-ray counts through a defined two-dimensional region and counts recorded at different locations on this region are considered to be transferred through a different channel. Therefore, a typical area detector has an array of channels to transfer and count the number of X-ray photons being received by the detector. The area detector should be able to measure a number of channels equal to at least the number of pixels in the diffraction image and many detectors measure many more channels than the number of pixels. If the number of channels exceeds the number of pixels in the image, typically the counts from several spatially adjacent channels are combined to form a single pixel value.

Figure 11:
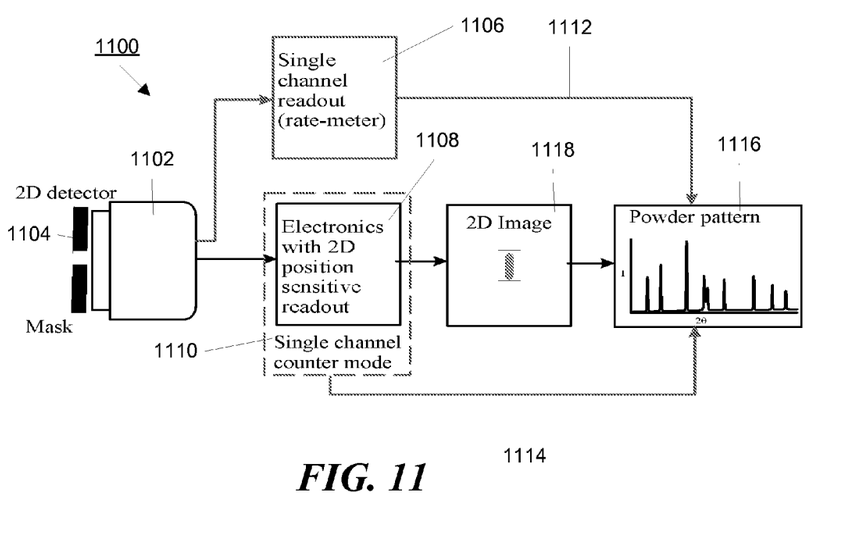
FIG. 11 is a block schematic diagram showing an area detector operating as a point detector and illustrating two different "single channel bypass" arrangements that can be used to allow X-rays to be counted without position information.

However, when an area detector is used as a point detector, the two-dimensional position of each X-ray count can be disregarded in order to increase the efficiency and speed of the system. When the area detector is operating as a point detector, a "single channel bypass" arrangement can be used to allow X-rays to be counted without position information. Such a system 1100 is shown in FIG. 11 which shows an area detector 1102 with a mask 1104. The single channel bypass can be separate detector electronics (such as a rate-meter 1106) which counts only the number of X-rays but ignores position information thereby producing a powder pattern 1116 as indicated schematically by arrow 1112, or the single channel bypass can be accomplished by a single channel counter mode 1110 of the area detection electronics 1108. In this latter arrangement the electronics can be switched between an area detection mode to produce a two-dimensional image 1118 and point detection mode to produce the powder pattern 1116 as indicated schematically be arrow 1114. Experimental results show that a single channel bypass arrangement can significantly increase the data acquisition speed so that the area detector 1102 can be used as a point detector with the same speed as a conventional point detector.

While the invention has been shown and described with reference to a number of embodiments thereof, it will be recognized by those skilled in the art that various changes in form and detail may be made herein without departing from the spirit and scope of the invention as defined by the appended claims.

What is claimed is:

1. A method for converting a two-dimensional X-ray diffractometer having an area detector with a two-dimensional detection region to detect X-rays diffracted from a sample into an X-ray diffractometer that uses a point detector, comprising:
    (a) providing a mask fabricated from a radiopaque material having a sufficient size to cover the entire two-dimensional detection region and a single opening therein through which X-rays diffracted from the sample can reach the area detector and which has an area substantially less than the two-dimensional detection region; and
    (b) mounting the mask over the detection region of the detector prior to measuring X-rays, such that the relative position of the mask and the detector remains fixed during said measuring.

2. The method of claim 1 wherein the X-ray diffractometer has a Bragg-Brentano geometry.

3. The method of claim 1 wherein the X-ray diffractometer has a parallel geometry.

4. The method of claim 1 wherein the X-ray diffractometer has a grazing incidence geometry.

5. The method of claim 1 further comprising mechanically attaching X-ray optics to the mask to process X-rays diffracted from the sample when the mask is attached to the area detector.

6. The method of claim 1 wherein the area detector has a curved two-dimensional detection region and step (a) comprises providing a mask with a curved surface that matches the curved two-dimensional detection region in order to reduce an X-ray beam path between the sample and the area detector.

7. The method of claim 1 wherein the mask has a center and wherein the opening in the mask is offset from the center of the mask.

8. The method of claim 7 further comprising attaching a monochromator to the mask so that X-rays diffracted from the sample pass through the monochromator before reaching the area detector.

9. The method of claim 1 further comprising detecting X-ray counts generated by the area detector without registering a position on the detector of the each X-ray count in order to increase detection speed.

10. Apparatus for converting a two-dimensional X-ray diffractometer having an area detector with a two-dimensional detection region to detect X-rays diffracted from a sample into an X-ray diffractometer that uses a point detector, comprising:
    a mask fabricated from a radiopaque material having a sufficient size to cover the entire two-dimensional detection region and a single opening therein through which X-rays diffracted from the sample can reach the area detector and which has an area substantially less than the two-dimensional detection region; and at least one removable fastener for mounting the mask over the detection region of the detector prior to measuring X-rays, such that the relative position of the mask and the detector remains fixed during said measuring.

11. The apparatus of claim 10 wherein the X-ray diffractometer has a Bragg-Brentano geometry.

12. The apparatus of claim 10 wherein the X-ray diffractometer has a parallel geometry.

13. The apparatus of claim 10 wherein the X-ray diffractometer has a grazing incidence geometry.

14. The apparatus of claim 10 further comprising X-ray optics that process X-rays diffracted from the sample and means for mechanically attaching the X-ray optics to the mask.

15. The apparatus of claim 10 wherein the area detector has a curved two-dimensional detection region and wherein the mask has a curved surface that matches the curved two-dimensional detection region in order to reduce an X-ray beam path between the sample and the area detector.

16. The apparatus of claim 10 wherein the mask has a center and the opening is offset from the center of the mask.

17. The apparatus of claim 16 further comprising a monochromator and means for attaching the monochromator to the mask so that X-rays diffracted from the sample pass through the monochromator before reaching the area detector.

18. The apparatus of claim 10 further a detector that detects X-ray counts generated by the area detector without registering a position on the detector of the each X-ray count in order to increase detection speed.

* * * * *